United States Patent [19]

Kawamura et al.

[11] Patent Number: 4,555,474
[45] Date of Patent: Nov. 26, 1985

[54] PHOTOPOLYMERIZABLE COMPOSITION

[75] Inventors: Kouichi Kawamura; Yoshimasa Aotani; Akira Umehara, all of Kanagawa, Japan

[73] Assignee: Fuji Photo Film Co., Ltd., Kanagawa, Japan

[21] Appl. No.: 697,813

[22] Filed: Feb. 4, 1985

[30] Foreign Application Priority Data

Feb. 2, 1984 [JP] Japan .................. 59-17339

[51] Int. Cl.⁴ .............................. G03C 1/68
[52] U.S. Cl. ................... 430/281; 430/920; 430/923; 204/159.18
[58] Field of Search ............ 430/281, 920, 923; 204/159.18

[56] References Cited

U.S. PATENT DOCUMENTS 3,870,524  3/1975  Watanabe et al. ............ 430/923
3,981,856  9/1976  Hudgin et al. ................ 526/351
4,171,977 10/1979  Hasegawa et al. ............ 430/281

FOREIGN PATENT DOCUMENTS 1504616  3/1978  United Kingdom .

Primary Examiner—Jack P. Brammer
Attorney, Agent, or Firm—Sughrue, Mion, Zinn, Macpeak & Seas

[57] ABSTRACT

A photopolymerizable composition is described, comprising a polymerizable compound having an ethylenically unsaturated bond and a photopolymerization initiator represented by formula (I)

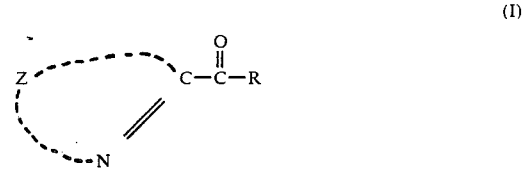

wherein Z represents a non-metallic atomic group forming a nitrogen-containing heterocyclic ring; and R represents a substituted or unsubstituted aryl group or a substituted or unsubstituted heterocyclic ring. The photopolymerization initiator (I) greatly improves the sensitivity of the composition.

20 Claims, No Drawings

PHOTOPOLYMERIZABLE COMPOSITION

FIELD OF THE INVENTION

This invention relates to a photopolymerizable composition comprising a polymerizable compound having an ethylenically unsaturated bond and a photopolymerization initiator; a binder and/or a sensitizer may also be present. More particularly, this invention relates to a photopolymerizable composition useful as a light-sensitive layer of a presensitized lithographic printing plate precursor, a photoresist, and the like.

BACKGROUND OF THE INVENTION

It is well known in the art that images can be reproduced by a photographic technique using a light-sensitive composition comprising a polymerizable compound having an ethylenically unsaturated bond, a photopolymerization initiator, and sometimes other components, such as an appropriate binder having a film forming property and a heat polymerization inhibitor. In this technique, a light-sensitive layer composed of the above-described light-sensitive composition is exposed to light through a mask of a desired pattern, thereby curing and insolubilizing the light-sensitive layer, and the unexposed areas are removed by an appropriate solvent to obtain a cured image of the desired pattern, as described, e.g., in U.S. Pat. Nos. 2,927,022, 2,902,356 and 3,870,524. It is very natural that this type of light-sensitive composition is useful for the production of lithographic printing plates or photoresists.

Use of a photopolymerization initiator in combination with the polymerizable compound has hitherto been proposed in order to increase light sensitivity of the light-sensitive composition since only the polymerizable compound having an ethylenically unsaturated bond is not sufficient to impart satisfactory light sensitivity to the composition. Such a photopolymerization initiator includes benzyl, benzoin, benzoin ethyl ether, Michler's ketone, anthraquinone, acridine, phenazine, benzophenone, 2-ethylanthraquinone, and the like.

However, use of these photopolymerization initiators cannot raise the curing rate of the photopolymerizable composition, thus requiring a longer time for imagewise exposure for image formation. Therefore, when a fine image is desired, even a slight vibration in operation leads to poor quality of images, and satisfactorily fine images cannot be obtained. Further, the quantity of energy emitted from a light source for exposure must be increased, so that considerations must be given to the evolution of a large quantity of heat associated with the increased energy. Furthermore, the light-sensitive layer is apt to be deformed or degraded due to such heat.

SUMMARY OF THE INVENTION

Accordingly, an object of this invention is to provide a photopolymerizable composition having high light sensitivity.

Another object of this invention is to provide a photopolymerizable composition containing a photopolymerization initiator which increases the photopolymerization rate of typically employed photopolymerizable compositions containing a polymerizable compound having an ethylenically unsaturated bond.

As a result of extensive investigations to achieve the above-described objects, it has now been found that a specific photopolymerization initiator significantly increases a photopolymerization rate of a polymerizable compound having an ethylenically unsaturated bond, and thus the present invention has been achieved.

More specifically, this invention relates to a photopolymerization composition comprising a polymerizable compound having an ethylenically unsaturated bond and a photopolymerization initiator represented by formula (I)

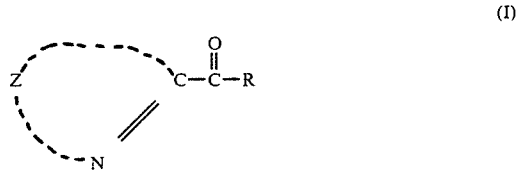

wherein Z represents a non-metallic atomic group forming a nitrogen-containing substituted or unsubstituted heterocyclic ring; and R represents a substituted or unsubstituted aryl group or a substituted or unsubstituted heterocyclic ring.

DETAILED DESCRIPTION OF THE INVENTION

The polymerizable compound having an ethylenically unsaturated bond which can be used in the present invention is a compound having at least one ethylenically unsaturated bond in its chemical structure and includes a monomer, a prepolymer (i.e., a dimer, a trimer, an oligomer, or a mixture thereof) and a copolymer thereof. Examples of these compounds are unsaturated carboxylic acids and their derivatives, such as salts, esters with aliphatic polyhydric alcohols, amides with aliphatic polyamine compounds, and the like.

Specific examples of the unsaturated carboxylic acids include acrylic acid, methacrylic acid, itaconic acid, crotonic acid, isocrotonic acid, maleic acid, etc.

The salts of the unsaturated carboxylic acids include sodium salts and potassium salts of the above-recited acids.

Specific examples of the esters between aliphatic polyhydric alcohols and the unsaturated carboxylic acids include acrylic esters, such as ethylene glycol diacrylate, triethylene glycol triacrylate, 1,3-butanediol diacrylate, tetramethylene glycol diacrylate, propylene glycol diacrylate, trimethylolpropane triacrylate, trimethylolethane triacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, sorbitol triacrylate, sorbitol tetraacrylate, sorbitol pentaacrylate, sorbitol hexaacrylate, polyester acrylate oligomers, etc.; methacrylic esters, such as tetramethylene glycol dimethacrylate, triethylene glycol dimethacrylate, trimethylolpropane trimethacrylate, trimethylolethane trimethacrylate, ethylene glycol dimethacrylate, pentaerythritol dimethacrylate, pentaerythritol trimethacrylate, dipentaerythritol dimethacrylate, sorbitol trimethacrylate, sorbitol tetramethacrylate, bis[p-(3-methacryloxy-2-hydroxypropoxy)phenyl]dimethylmethane, bis[p-(3-acryloxyethoxy)phenyl]dimethylmethane, etc.; itaconic esters, such as ethylene glycol diitaconate, propylene glycol diitaconate, 1,3-butanediol diitaconate, 1,4-butanediol diitaconate, tetramethylene glycol diitaconate, pentaerythritol diitaconate, sorbitol tetraitaconate, etc.; crotonic esters, such as ethylene glycol dicrotonate, tetramethylene glycol dicrotonate, pentaerythritol dicrotonate, sorbitol tetracrotonate, etc.; isocrotonic esters, such as ethylene glycol diisocrotonate, pentaerythritol diisocrotonate, sorbitol tetraisocrotonate, etc.; and maleic esters, such as ethylene glycol dimaleate, triethylene glycol dimaleate, pentaerythritol dimaleate, sorbitol tetramaleate, etc. Mixtures of these esters may also be used.

Specific examples of the amides between aliphatic polyamine compounds are methylenebis-acrylamide, methylenebis-methacrylamide, 1,6-hexamethylenebis-acrylamide, 1,6-hexamethylenebis-methacrylamide, diethylenetriamine trisacrylamide, xylylenebis-acrylamide, xylylenebis-methacrylamide, and the like.

In addition, vinylurethane compounds having two or more polymerizable vinyl groups in their molecule which are obtained by adding a vinyl monomer having a hydroxyl group represented by the formula

CH$_2$=C(R)COOCH$_2$CH(R')OH wherein R and R' each represents a hydrogen atom or a methyl group, to a polyisocyanate compound having two or more isocyanato groups in its molecule, as disclosed in Japanese Patent Publication No. 41708/73, may also be used as polymerizable compounds.

The photopolymerization initiator which can be used in the photopolymerizable composition according to the present invention will be described below.

In the above-described formula (I), the nitrogen-containing heterocyclic ring which is formed by Z with the adjacent N=C bond includes, for example, thiazoles, e.g., benzothiazole, α-naphthothiazole, β-naphthothiazole, etc.; oxazoles, e.g., benzoxazole, β-naphthoxazole, etc.; selenazoles, e.g., benzoselenazole, etc.; imidazoles, e.g., imidazole, benzimidazole, etc.; isoindoles, e.g., 3,3-dimethylindolenine, etc.; quinolines, e.g., quinoline, isoquinoline, etc.; diazoles, e.g., 1,3,4-oxadiazole, 1,3,4-thiadiazole, 1,3,4-selenadiazole, etc.; triazoles, e.g., 1,2,4-triazole, etc.; pyrazine; quinoxaline; s-triazine; phenanthrazine; and the like. Substituents for the substituted nitrogen-containing heterocyclic ring include an alkyl group having from 1 to 6 carbon atoms, e.g., a methyl group, an ethyl group, etc.; an alkoxy group having from 1 to 6 carbon atoms, e.g., a methoxy group, an ethoxy group, etc.; a halogen atom, e.g., a chlorine atom, a bromine atom, etc.; a cyano group; an amino group; an amino group substituted with an alkyl group of from 1 to 4 carbon atoms, e.g., a dimethylamino group, etc.; a carboalkoxy group having from 1 to 4 carbon atoms in its alkyl moiety, e.g., a carbomethoxy group, etc.; a substituted or unsubstituted aryl group having from 6 to 10 carbon atoms, e.g., a phenyl group, a p-methoxyphenyl group, a p-chlorophenyl group, etc.; and the like.

In formula (I), the aryl group as represented by R is a group derived from a mono- or polycyclic compound having from 6 to 14 carbon atoms, such as a phenyl group, a naphthyl group, etc. Substituents for the substituted aryl group can include an alkyl group of from 1 to 6 carbon atoms, an alkoxy group of from 1 to 6 carbon atoms, an aryl group of from 6 to 10 carbon atoms, an amino group, an amino group substituted with an alkyl group of from 1 to 6 carbon atoms, an amino group substituted with an acyl group of from 1 to 6 carbon atoms, a cyano group, a halogen atom, e.g., a fluorine atom, etc., and the like. The alkyl group herein used as a substituent includes an alkyl group and a substituted alkyl group substituted with an alkoxy group of from 1 to 2 carbon atoms, e.g., a methoxy group and an ethoxy group, or a halogen atom, e.g., a chlorine atom.

Of these substituents for the aryl group, the preferred are an alkyl group of from 1 to 4 carbon atoms, e.g., a methyl group, an ethyl group, etc.; an alkoxy group of from 1 to 4 carbon atoms, e.g., a methoxy group, an ethoxy group, etc.; an amino group substituted with an alkyl group of from 1 to 4 carbon atoms, e.g., a dimethylamino group, a diethylamino group, etc.; an amino group substituted with an acyl group of from 1 to 4 carbon atoms, and a halogen atom, e.g., a fluorine atom, a chlorine atom, a bromine atom, etc.

The heterocyclic group as represented by R is a group derived from a mono- or polycyclic compound containing at least any one of nitrogen, oxygen and sulfur atoms, and preferably a 5- or 6-membered heterocyclic aromatic compound, e.g., furan, pyrrole, pyridine, etc.

Substituents for the heterocyclic group R include the same groups as enumerated as substituents for the aryl group.

Preferred among the compounds represented by formula (I) are those represented by formula (II)

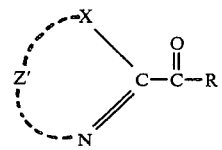

(II)

wherein R is the same as defined for formula (I); Z' represents a nom-metallic atom group forming a nitrogen-containing heterocyclic ring together with X; and X represents O, S or N—R', wherein R' represents a hydrogen atom, a substituted or unsubstituted alkyl group having from 1 to 4 carbon atoms or a substituted or unsubstituted aryl group having from 6 to 10 carbon atoms.

Typical examples of the compounds represented by the above-described formula (II) include thiazoles, oxazoles, imidazoles, oxadiazoles, triazoles, and the like.

These photopolymerization initiators of above-described formula (I) can be synthesized in accordance with known processes.

For example, one process comprises reacting a compound represented by formula (III)

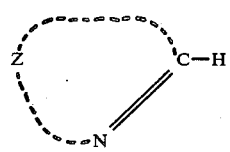

(III)

wherein Z is the same as defined for formula (I), with a compound represented by formula (IV)

(IV)

wherein R is the same as defined for formula (I), as disclosed in T. Caronna, et al., *Journal of the Chemical Society*, Perkin II, 2035–2038 (1972) and *Journal of the Chemical Society* (C), 1747–1750 (1971).

Another process for synthesizing the compounds of formula (II) comprises reacting a compound represented by formula (V)

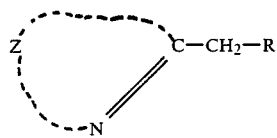

(V)

wherein Z and R are the same as defined for formula (I), with sulfonyl chloride, or with an oxidizing agent such as selenium dioxide, as disclosed in E. Müller, et al., *Liebigs Annalen der Chemie*, Vol. 73, 87–95 (1968).

Specific examples of photopolymerization initiators of formula (I) which can be used in the present invention are shown below.

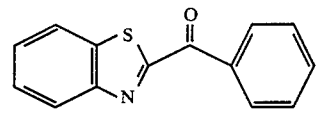 No. 1

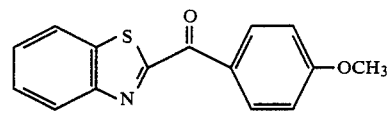 No. 2

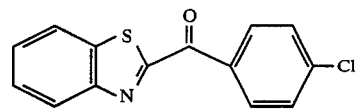 No. 3

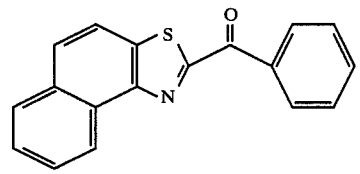 No. 4

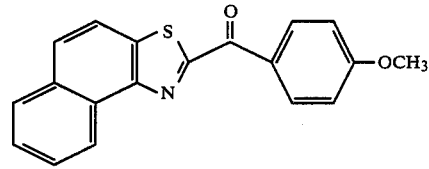 No. 5

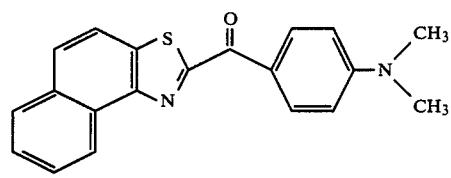 No. 6

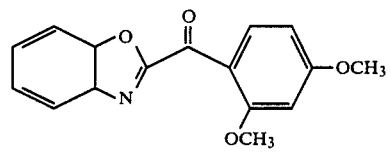 No. 7

-continued

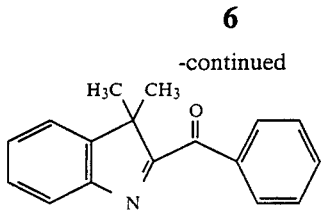 No. 8

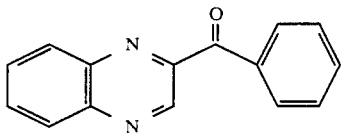 No. 9

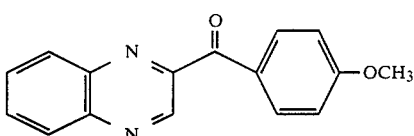 No. 10

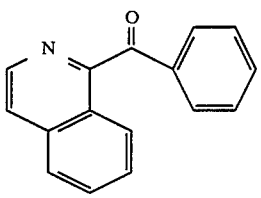 No. 11

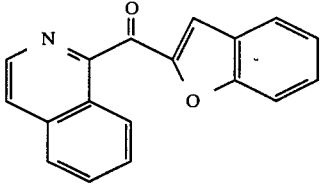 No. 12

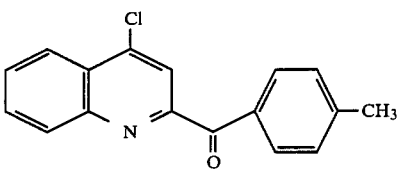 No. 13

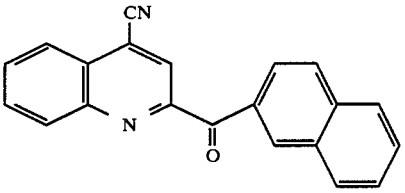 No. 14

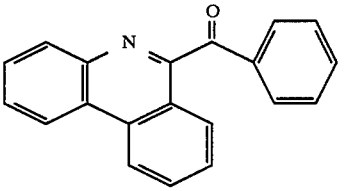 No. 15

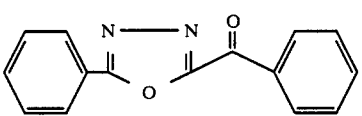 No. 16

-continued

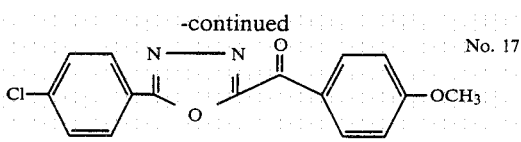
No. 17

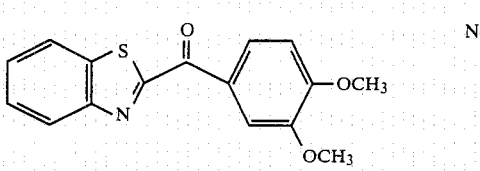
No. 18

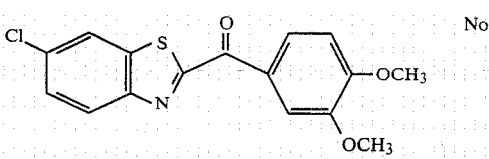
No. 19

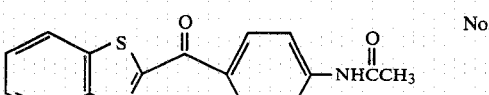
No. 20

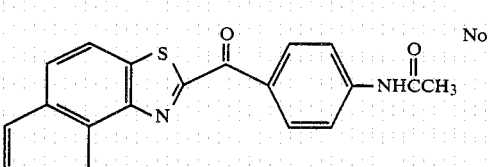
No. 21

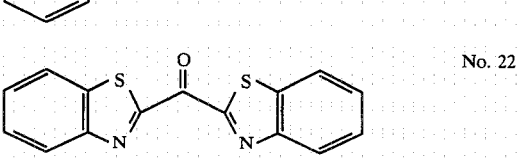
No. 22

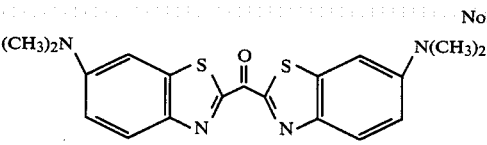
No. 23

If desired, the photopolymerizable composition according to the present invention can contain a binder. The binders to be used should meet several conditions. The compatibility with the polymerizable compound containing an ethylenically unsaturated bond and the photopolymerization initiator should be such that the binder does not separate from the composition comprising the above-described components in the production of light-sensitive materials from the preparation of the composition to the application of the composition and subsequent drying. The binder should be removable after light exposure either through dissolution in a solvent or peeling off from a light-sensitive layer or resist layer to thereby effect development processing according to a particular use. Further, the binder should have appropriate additional properties, such as a property to form a rigid film as a light-sensitive layer or a resist layer. Such a binder can usually be selected from linear organic high polymers. Specific examples of the binders include chlorinated polyolefins, such as chlorinated polyethylene, chlorinated polypropylene, etc.; polyacrylic alkyl esters (the alkyl group includes a methyl group, an ethyl group, an n-butyl group, an isobutyl group, an n-hexyl group, a 2-ethylhexyl group, etc.); copolymers of an acrylic alkyl ester (the alkyl group is the same as above) with at least one monomer, e.g., acrylonitrile, vinyl chloride, vinylidene chloride, styrene, butadiene, etc.; polyvinyl chloride; copolymers of vinyl chloride and acrylonitrile; polyvinylidene chloride; copolymers of vinylidene chloride and acrylonitrile; polyvinyl acetate; polyvinyl alcohol, polyacrylonitrile; copolymers of acrylonitrile and styrene; copolymers of acrylonitrile, butadiene and styrene; polymethacrylic alkyl esters (the alkyl group can include a methyl group, an ethyl group, an n-propyl group, an n-butyl group, an isobutyl group, an n-hexyl group, a cyclohexyl group, a 2-ethylhexyl group, etc.); copolymers of a methacrylic alkyl ester (the alkyl group is the same as above) with at least one monomer, e.g., acrylonitrile, vinyl chloride, vinylidene chloride, styrene, butadiene, etc.; polystyrene; poly-α-methylstyrene; polyamide (e.g., nylon 6, nylon 6,6, etc.); methyl cellulose; ethyl cellulose; acetyl cellulose; polyvinyl formal; polyvinyl butyral; and the like.

Moreover, use of an organic high polymeric binder which is soluble in water or an alkaline aqueous solution makes it possible to conduct development with water or an alkaline aqueous solution as a developer. Such a high polymeric binder includes addition polymers having a carboxylic acid moiety in their side chains, for example, copolymers of methacrylic acid with methyl methacrylate, ethyl methacrylate, butyl methacrylate, benzyl methacrylate, ethyl acrylate, ethyl methacrylate and styrene, or the like; copolymers of acrylic acid with ethyl acrylate, butyl acrylate, ethyl acrylate and styrene, or a like monomer; itaconic acid copolymers; crotonic acid copolymers; partially esterified maleic acid copolymers; and the like; and also acidic cellulose derivatives having a carboxyl group in their side chains.

These polymers may be used as a binder either individually or as a mixture of two or more thereof in any proportions as long as they are compatible with each other to such an extent that they do not separate in the production processes from the preparation of the coating solution through drying.

The high polymers used as binders may have a wide range of molecular weight depending on the kind of the polymer, but is generally from 5,000 to 2,000,000, and preferably from 10,000 to 1,000,000.

The photopolymerizable composition according to the present invention may further contain a sensitizer, if desired. The sensitizer to be used can be selected from those which increase the range of photopolymerization when used in combination with the photopolymerization initiator represented by formula (I).

Such sensitizers specifically include carbonyl compounds, e.g., benzoin, benzoin methyl ether, benzoin ethyl ether, 2,2-dimethoxy-2-phenylacetophenone, benzoyl-1-cyclohexanol, 2-morpholino-2-methyl-p-methylthiopropiophenone, 2-hydroxy-2-methyl-p-chloropropiophenone, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-anthraquinone, 2,6-dichloro-9,10-anthraquinone, xanthone, 2-methylxanthone, 2-methoxyxanthone, thioxanthone, benzyl, dibenzalacetone, p-(dimethylamino)phenyl styryl ketone, p-(dimethylamino)phenyl p-methylstyryl ketone, benzophenone, p-(dimethylamino)benzophenone (or Michler's ketone), p-(diethylamino)benzophenone, benzanthrone, and the like. Of these, Michler's ketone and 2-morpholino-2-methyl-p-methylthiopropiophenone are the most preferred.

In addition, compounds represented by the following formula (VI) as disclosed in U.S. Pat. No. 3,870,524 can also be used as preferred sensitizers in the present invention:

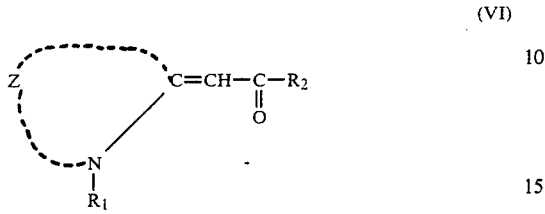

wherein $R_1$ represents an alkyl group (e.g., a methyl group, an ethyl group, a propyl group, etc.) or a substituted alkyl group (e.g., a 2-hydroxyethyl group, a 2-methoxyethyl group, a carboxymethyl group, a 2-carboxyethyl group, etc.); $R_2$ represents an alkyl group (e.g., a methyl group, an ethyl group, etc.) or an aryl group (e.g., a phenyl group, a p-hydroxyphenyl group, a naphthyl group, a thienyl group, etc.); and Z represents a non-metallic atom group necessary to form a nitrogen-containing heterocyclic nucleus which is usually used in cyanine dyes, such as benzothiazoles (e.g., benzothiazole, 5-chlorobenzothiazole, 6-chlorobenzothiazole, etc.), naphthothiazoles (e.g., α-naphthothiazole, β-naphthothiazole, etc.), benzoselenazoles (e.g., benzoselenazole, 5-chlorobenzoselenazole, 6-methoxybenzoselenazole, etc.), naphthoselenazoles (e.g., α-naphthoselenazole, β-naphthoselenazole, etc.), benzoxazoles (e.g., benzoxazole, 5-methylbenzoxazole, 5-phenylbenzoxazole, etc.), naphthoxazoles (e.g., α-naphthoxazole, β-naphthoxazole, etc.), and the like.

Specific examples of compounds represented by formula (VI) are disclosed in U.S. Pat. No. 3,870,524. Therefore, sensitizers to be used in the present invention can appropriately be selected from the known compounds.

Further, sensitizers disclosed in U.S. Pat. No. 4,062,686, such as 2-[bis(2-furoyl)methylene]-3-methylbenzothiazoline, 2-[bis(2-thienyl)methylene]-3-methylbenzothiazoline, 2-[bis(2-furoyl)methylene]-3-methylnaphtho[1,2-d]thiazoline, etc., can also be used as preferred sensitizers in the present invention.

Furthermore, the following compounds can also be used as preferred sensitizers in the present invention:

(i) Halogen compounds described in the British Pat. No. 1,234,648, U.S. Pat. No. 3,905,813 and Japanese Patent Application (OPI) Nos. 24113/80 and 15503/83 (U.S. patent application Ser. No. 400,200, filed July 20, 1982) (the term "OPI" as used herein refers to a "published unexamined Japanese patent application"). Typical examples of these compounds are 2,6-di(trichloromethyl)-4-(p-methoxyphenyl)-1,3,5-triazine, 2-trichloromethyl-5-(p-methoxystyryl)-1,3,4-oxadiazole, anthraquinone-1-sulfonyl chloride, and the like.

(ii) Amino compounds described in M. R. Sander, et al., *Journal of Polymer Society*, Vol. 10, 3173 (1972), and Japanese Patent Application (OPI) Nos. 82102/76 and 134692/77. Typical examples of these compounds are trimethylamine, triethanolamine, ethyl p-dimethylaminobenzoate, N-phenylglycine, and the like.

(iii) Phosphorous ester compounds described in West German Patent Application (OLS) No. 2,528,358, such as triethyl phosphite.

(iv) Mercapto compounds described in U.S. patent application Ser. No. 617,436, filed June 5, 1984, such as 2-mercaptobenzimidazole, etc.

(v) Sulfonyloxime compounds described in West German Patent Application (OLS) No. 3,410,387 and U.S. Pat. No. 4,258,121. Typical examples of these compounds are 2-styryl-3-phenylsulfonyloxy-4(3H)-quinazoline, N-hydroxy-1,8-naphthalimidobenzenesulfonic acid ester, and the like.

(vi) Hexaarylbiimidazole compounds described in Japanese Patent Publication No. 37377/70. Typical examples of these compounds are 2,2'-bis(o-chlorophenyl)-4,4',5,5'-tetraphenylbiimidazole, 2,2'-bis-(o,p-dichlorophenyl)-4,4',5,5'-tetraphenylbiimidazole, and the like.

It is desirable to add a thermal polymerization inhibitor to the photopolymerizable composition of the present invention in order to prevent unnecessary thermal polymerization of the polymerizable compound having an ethylenically unsaturated bond during the preparation or storage of the composition. The thermal polymerization inhibitors which can be suitably used in the present invention include hydroquinone, p-methoxyphenol, di-t-butyl-p-cresol, pyrogallol, t-butyl catechol, benzoquinone, cuprous chloride, phenothiazine, chloranil, naphthylamine, β-naphthol, nitrobenzene, dinitrobenzene, etc.

If desired, the photopolymerizable composition of the present invention may contain dyes or pigments for coloration, such as Methylene Blue, Crystal Violet, Rhodamine B, Fuchsine, Auramine, azo dyes, anthraquinone dyes, titanium oxide, carbon black, iron oxide, phthalocyanine pigments, azo pigments, and the like.

The photopolymerizable composition of the present invention may further contain a plasticizer, if desired. Plasticizers which can be used include phthalic esters, e.g., dimethyl phthalate, diethyl phthalate, dibutyl phthalate, dihexyl phthalate, dicyclohexyl phthalate, ditridecyl phthalate, etc.; glycol esters, e.g., dimethyl glycol phthalate, ethylphthalyl ethylglycolate, butylphthalyl butylglycolate, etc.; phosphoric esters, e.g., tricresyl phosphate, triphenyl phosphate, etc.; aliphatic dibasic acid esters, e.g., diisobutyl adipate, dioctyl adipate, dibutyl sebacate, dibutyl maleate, etc.; and the like.

The photopolymerizable composition according to the present invention can be obtained by dissolving the above-described various components in a solvent, and the resulting coating solution can be applied to an appropriate support using known coating methods. Preferred and more preferred proportions of the components per 100 parts by weight of the polymerizable compound having an ethylenically unsaturated bond are shown below.

| Component | Preferred Proportion (parts by weight) | More Preferred Proportion (parts by weight) |
| --- | --- | --- |
| Photopolymerization Initiator | 0.01–50 | 0.1–10 |
| Binder | 0–1,000 | 0–500 |
| Sensitizer | 0–100 | 0–20 |
| Thermal Polymerization Inhibitor | 0–10 | 0–5 |
| Dye or Pigment | 0–50 | 0–20 |

| Component | Preferred Proportion (parts by weight) | More Preferred Proportion (parts by weight) |
|---|---|---|
| Plasticizer | 0–200 | 0–50 |

The solvent used for coating the photopolymerizable composition includes, for example, ethylene dichloride, cyclohexanone, methyl ethyl ketone, methyl cellosolve, ethyl cellosolve, methyl cellosolve acetate, monochlorobenzene, toluene, xylene, ethyl acetate, butyl acetate, and the like. These solvents may be used alone or in combination thereof.

In the production of presensitized lithographic printing plates, the photopolymerizable composition of the invention is applied to a support in an amount of from 0.1 to 10.0 g/m$^2$, and preferably from 0.5 to 5.0 g/m$^2$.

The photopolymerizable composition in accordance with the present invention is suitable as a light-sensitive layer of presensitized lithographic printing plates. Supports suitable for presensitized lithographic printing plates include an aluminum plate that has been rendered hydrophilic, e.g., a silicate-treated aluminum plate, an anodically oxidized aluminum plate, an aluminum plate on which a silicate is electrode-deposited, etc., a zinc plate, a stainless steel plate, a chromium-treated copper plate, a plastic film that has been rendered hydrophilic, paper, and the like.

When the photopolymerizable composition of the present invention is used as a photoresist, supports therefor can include various materials, such as a copper-plated plate, a stainless steel plate, a glass plate, etc.

The present invention will now be illustrated in greater detail by way of Synthesis Examples for synthesizing the photopolymerization initiator used in the present invention and Examples, but it should be understood that these Synthesis Examples and Examples are not limiting the present invention.

SYNTHESIS EXAMPLE 1

Preparation of 2-(p-Methoxybenzoyl)benzothiazole (Compound No. 2)

13.5 g of benzothiazole and 40.8 g of anisaldehyde were dissolved in a mixed solvent comprising 50 ml of water and 150 ml of acetic acid and containing 2.8 ml of concentrated hydrochloric acid, and the resulting solution was cooled to 0° C.

A solution of 83.4 g of ferrous sulfate heptahydrate in 150 ml of water and 38.7 g of t-butyl hydroperoxide were simultaneously added dropwise to the above-prepared solution over a period of 15 minutes while stirring. After the addition, the stirring was continued for 45 minutes, and then the precipitated crystals were collected by filtration. The resulting crude crystals were recrystallized twice from ethanol to provide 16.7 g of crystals having a melting point of 124° to 125° C. Yield: 61%.

The resulting crystals were confirmed to be 1-(p-methoxybenzoyl)benzothiazole from the melting point identical to that reported (i.e., 125° C.) in *Journal of Chemical Society* (C), 1749 (1971).

SYNTHESIS EXAMPLE 2

Preparation of 2-Benzoyl-β-naphthothiazole (Compound No. 4)

9.4 g of β-naphthothiazole and 15.3 g of benzaldehyde were added to a mixed solution comprising 25 ml of water and 150 ml of acetic acid and containing 1.4 ml of concentrated sulfuric acid, and the mixture was heated at 36° C. to form a uniform solution.

A solution comprising 41.7 g of ferric sulfate heptahydrate and 75 ml of water and 19.4 g of t-butyl hydroperoxide were simultaneously added dropwise to the above-prepared solution over a period of 20 minutes while stirring.

After the addition, the stirring was further continued for 2 hours at room temperature, and the thus formed solid was collected by filtration. Recrystallization from ethyl acetate yielded 5.36 g of grown needle crystals having a melting point of 133° to 134° C. Yield: 37%.

Elementary Analysis for $C_{18}H_{11}NOS$: Calcd. (%): C 74.72, H 3.83, N 4.84. Found (%): C 74.93, H 3.90, N 4.65.

SYNTHESIS EXAMPLE 3

Preparation of 3-Phenyl-5-benzoyl-1,3,4-oxadiazole (Compound No. 16)

23.6 g of 2-phenyl-5-benzyl-1,3,4-oxadiazole was dissolved in a mixed solvent of 200 ml of sulfuryl chloride and 200 ml of acetic acid, and the mixture was heated under reflux for 6 hours. The reaction mixture was poured into 1.5 liters of water, and the mixture was heated on a steam bath for 1 hour, followed by cooling. The thus-formed crystals were collected by filtration and recrystallized from ethanol to obtain 21.49 g of colorless needle crystals having a melting point of 139° to 141° C. Yield: 86%.

Elementary Analysis for $C_{15}H_{10}N_2O_2$: Calcd. (%): C 71.99, H 4.03, N 11.19. Found (%): C 72.03, H 3.83, N 11.20.

Mass Spectrum: m/e: 250 (M+), 145, 105.

EXAMPLES 1 TO 4 AND COMPARATIVE EXAMPLES 1 TO 3

Light-sensitive compositions of the following formulation, in which photopolymerization initiators as indicated in Table 1 were used, were coated on aluminum sheets that had been grained with a nylon brush followed by being subjected to silicate treatment by the use of a rotary coating machine at 200 rpm. The coating layers were dried at 100° C. for 5 minutes to form light-sensitive layers havng a dry film thickness of about 2 microns, to thereby prepare light-sensitive sheets.

Light-Sensitive Composition Formulation

Benzyl Methacrylate-Methacrylic Acid Copolymer (molar ratio: 73:27): 5.0 g
Pentaerythritol Tetraacrylate: 3.6 g
Photopolymerization Initiator: 0.12 g
Methyl Ethyl Ketone: 20 g
Methyl Cellosolve Acetate: 20 g The thus prepared light-sensitive sheet was exposed to light emitted from a 2 kw ultrahigh pressure mercury lamp for 16 seconds through a step wedge having 15 density steps with a density difference of 0.15 by using a vacuum printing apparatus. After the exposure, the light-sensitive sheet was developed with a developing solution of the following formulation.

Developing Solution Formulation

Sodium Tertiary. Phosphate: 25 g
Sodium Primary Phosphate: 5 g
Butyl Cellosolve: 70 g
Activator: 2 ml Water: 1,000 ml The highest of the steps of the step wedge to which the resulting image corresponded was taken as the sensitivity of the sample, and the results obtained are shown in Table 1. A higher step indicates higher sensitivity.

For comparison, the same procedures as described above were repeated except that the photopolymerization initiator of the present invention was replaced by benzophenone (Comparative Example 1) or 4-benzoylpyridine (Comparative Example 2) or no photopolymerization initiator was used (Comparative Example 3). The results are also shown in Table 1.

TABLE 1

| Example No. | Photopolymerization Initiator | Highest Step of Step Wedge |
|---|---|---|
| 1 | Compound No. 1 | 2 |
| 2 | Compound No. 2 | 4 |
| 3 | Compound No. 4 | 6 |
| 4 | Compound No. 10 | 3 |
| Comparative Example 1 | Benzophenone | 0 |
| Comparative Example 2 | 4-Benzoylpyridine | 0 |
| Comparative Example 3 | None | 0 |

As shown in Table 1, the light-sensitive composition using the photopolymerizaton initiator in accordance with the present invention shows higher sensitivity as compared with Comparative Examples, indicating that the desired effects can be obtained.

EXAMPLES 5 TO 11 AND COMPARATIVE EXAMPLES 4 TO 6

A light-sensitive composition was prepared in the same manner as described in Example 1 except for using a photopolymerization initiator as indicated in Table 2 and adding 0.14 g of Michler's ketone as a sensitizer. A light-sensitive sheet was prepared, exposed to light, and subjected to development in the same manner as in Example 1. The highest of the steps of the step wedge to which the resulting image corresponded, is shown in Table 2 as sensitivity of the respective light-sensitive samples. For comparison, the same procedures as described above were repeated except for using benzophenone or 4-benzoylpyridine in place of the photopolymerization initiator of the present invention (Comparative Example 4 or 5) or using only Michler's ketone with no photopolymerization initiator (Comparative Example 6). The results obtained are also shown in Table 2.

TABLE 2

| Example No. | Photopolymerization Initiator | Highest Step of Step Wedge |
|---|---|---|
| 5 | Compound No. 1 | 15 |
| 6 | Compound No. 2 | 15 |
| 7 | Compound No. 3 | 14 |
| 8 | Compound No. 5 | 15 |
| 9 | Compound No. 9 | 12 |
| 10 | Compound No. 16 | 15 |
| 11 | Compound No. 17 | 14 |
| Comparative Example 4 | Benzophenone | 10 |
| Comparative Example 5 | 4-Benzoylpyridine | 11 |
| Comparative Example 6 | None | 4 |

As is apparent from Table 2, samples in which Michler's ketone is used in combination with the photopolymerization initiator according to the present invention exhibit greatly improved sensitivity as compared with Comparative Example 6 in wich Michler's ketone is used alone. Further, comparison between Table 1 (Examples 1 to 4) and Table 2 indicates that Michler's ketone acts as an effective sensitizer in the case of using a photopolymerization initiator represented by formula (I) according to the present invention.

EXAMPLES 12 TO 14

A compound having the structure as shown in Table 3 was added as a sensitizer to the same light-sensitive composition as used in Example 1 to prepare three kinds of coating compositions.

TABLE 3

| Sensitizer | Structure | Amount Added (g) |
|---|---|---|
| A | 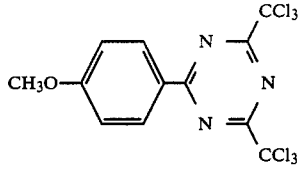 | 0.22 |
| B | 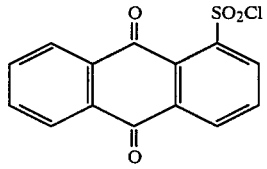 | 0.16 |
| C | 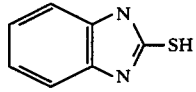 | 0.08 |

A light-sensitive sheet was produced in the analogous manner as described in Example 1, but using the above-prepared compositions. The resulting samples were exposed to light and developed in the same manner as in Examples 1 to 4 to evaluate sensitivity. The results obtained are shown in Table 4.

For comparison, the same procedures as above were repeated except for using no photopolymerization initiator, and the results are also shown in Table 4.

TABLE 4

| Example No. | Sensitizer | Photopolymerization Initiator | Highest Step of Step Wedge |
|---|---|---|---|
| 12 | A | Compound No. 1 | 15 |
| 13 | B | Compound No. 1 | 15 |
| 14 | C | Compound No. 1 | 13 |
| Comparative Example 7 | A | None | 12 |
| Comparative Example 8 | B | None | 11 |
| Comparative Example 9 | C | None | 3 |

It can be seen from Table 4 that incorporation of Sensitizers A, B and C to photopolymerizable compositions containing the photopolymerization initiator of the present invention greatly improves sensitivity of the composition.

While the invention has been described in detail and with reference to specific embodiments thereof, it will be apparent to one skilled in the art that various changes and modifications can be made therein without departing from the spirit and scope thereof.

What is claimed is:

1. A photopolymerizable composition comprising a polymerizable compound having an ethylenically unsaturated bond and a photopolymerization initiator represented by formula (I)

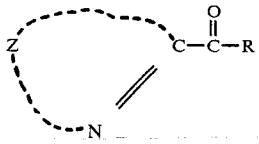
(I)

wherein Z represents a non-metallic atomic group forming a substituted or unsubstituted nitrogen-containing heterocyclic ring; and R represents a substituted or unsubstituted aryl group or a substituted or unsubstituted heterocyclic ring.

2. A photopolymerizable composition as in claim 1, wherein the composition further comprises a binder.

3. A photopolymerizable composition as in claim 1, wherein the composition further comprises a sensitizer.

4. A photopolymerizable composition as in claim 1, wherein the photopolymerization initiator is represented by formula (II)

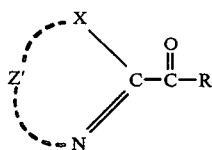
(II)

wherein Z' represents a non-metallic atomic group forming a nitrogen-containing substituted or unsubstituted heterocyclic ring together with X; X represents O, S, or N—R', wherein R' represents a substituted or unsubstituted alkyl group having from 1 to 4 carbon atoms or a substituted or unsubstituted aryl group having from 6 to 10 carbon atoms; and R represents a substituted or unsubstituted aryl group or a substituted or unsubstituted heterocyclic ring.

5. A photopolymerizable composition as in claim 1, wherein the photopolymerization initiator is present in an amount of from 0.01 to 50 parts by weight per 100 parts by weight of the polymerizable compound.

6. A photopolymerizable composition as in claim 1, wherein the photopolymerization initiator is present in an amount of from 0.1 to 10 parts by weight per 100 parts by weight of the polymerizable compound.

7. A photopolymerizable composition as in claim 2, wherein the binder is present in an amount of up to 1,000 parts by weight per 100 parts by weight of the polymerizable compound.

8. A photopolymerizable composition as in claim 7, wherein the binder is present in an amount of up to 500 parts by weight per 100 parts by weight of the polymerizable compound.

9. A photopolymerizable composition as in claim 3, wherein the sensitizer is present in an amount of up to 100 parts by weight per 100 parts by weight of the polymerizable compound.

10. A photopolymerizable composition as in claim 9, wherein the sensitizer is present in an amount of up to 20 parts by weight per 100 parts by weight of the polymerizable compound.

11. A photopolymerizable composition as in claim 2, wherein the photopolymerization initiator is represented by formula (II)

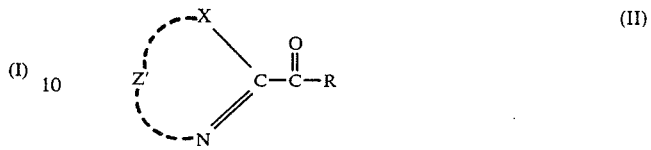
(II)

wherein Z' represents a non-metallic atomic group forming a nitrogen-containing substituted or unsubstituted heterocyclic ring together with X; X represents O, S, or N—R', wherein R' represents a substituted or unsubstituted alkyl group having from 1 to 4 carbon atoms or a substituted or unsubstituted aryl group having from 6 to 10 carbon atoms; and R represents a substituted or unsubstituted aryl group or a substituted or unsubstituted heterocyclic ring.

12. A photopolymerizable composition as in claim 2, wherein the photopolymerization initiator is present in an amount of from 0.01 to 50 parts by weight per 100 parts by weight of the polymerizable compound.

13. A photopolymerizable composition as in claim 2, wherein the photopolymerization initiator is present in an amount of from 0.1 to 10 parts by weight per 100 parts by weight of the polymerizable compound.

14. A photopolymerizable composition as in claim 3, wherein the photopolymerization initiator is represented by formula (II)

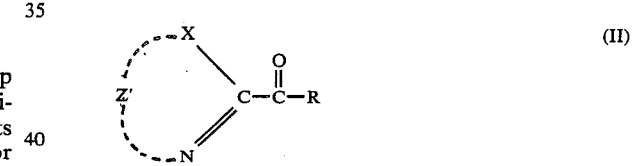
(II)

wherein Z' represents a non-metallic atomic group forming a nitrogen-containing substituted or unsubstituted heterocyclic ring together with X; X represents O, S, or N—R', wherein R' represents a substituted or unsubstituted alkyl group having from 1 to 4 carbon atoms or a substituted or unsubstituted aryl group having from 6 to 10 carbon atoms; and R represents a substituted or unsubstituted aryl group or a substituted or unsubstituted heterocyclic ring.

15. A photopolymerizable composition as in claim 3, wherein the photopolymerization initiator is present in an amount of from 0.01 to 50 parts by weight per 100 parts by weight of the polymerizable compound.

16. A photopolymerizable composition as in claim 3, wherein the photopolymerization initiator is present in an amount of from 0.1 to 10 parts by weight per 100 parts by weight of the polymerizable compound.

17. A photopolymerizable composition as in claim 1, wherein the composition further comprises a binder present in an amount of up to 1,000 parts by weight, and a sensitizer present in an amount of up to 100 parts by weight, per 100 parts by weight of the polymerizable compound.

18. A photopolymerizable composition as in claim 4, wherein the composition further comprises a binder present in an amount of up to 1,000 parts by weight, and a sensitizer in an amount of up to 100 parts by weight, per 100 parts by weight of the polymerizable compound.

19. A photopolymerizable composition as in claim 3, wherein said sensitizer is a carbonyl compound, a halogen compound or an amino compound.

20. A photopolymerizable composition as in claim 19, wherein said sensitizer is 2-morpholino-2-methyl-p-methylthiopropiophenone, Michler's ketone, 2,6-di(trichloromethyl)-4-(p-methoxyphenyl)-1,3,5-triazine, 2-trichloromethyl-5-(p-methoxystyryl)-1,3,4-oxadiazole, anthraquinone-1-sulfonyl chloride, trimethylamine, triethanolamine, ethyl p-dimethylaminobenzoate or N-phenylglycine.

* * * * *